US00PP19665P2

(12) United States Plant Patent
Ronald

(10) Patent No.: US PP19,665 P2
(45) Date of Patent: Jan. 27, 2009

(54) AMUR CHERRY TREE NAMED 'JEFSPUR'

(50) Latin Name: *Prunus maackii*
Varietal Denomination: Jefspur

(76) Inventor: Philip Ronald, P.O. Box 402, Portage la Prairie, Manitoba RIN 3B7 (CA)

( * ) Notice: Subject to any disclaimer, the term of this patent is extended or adjusted under 35 U.S.C. 154(b) by 0 days.

(21) Appl. No.: 11/985,234

(22) Filed: Nov. 14, 2007

(51) Int. Cl.
*A01H 5/00* (2006.01)

(52) U.S. Cl. ..... Plt./182
(58) Field of Classification Search ..... Plt./182
See application file for complete search history.

(56) References Cited

PUBLICATIONS

UPOV–ROM GTITM, Plant Variety Database, 2007,/06, GTI Jouve Retrieval Software, Citation for amur cherry tree 'Jefspur'.*

* cited by examiner

*Primary Examiner*—Annette H Para
*Assistant Examiner*—S. B. McCormick-Ewoldt
(74) *Attorney, Agent, or Firm*—Penny J. Aguirre

(57) ABSTRACT

A new cultivar of *Prunus maackii,* 'Jespur', characterized by its dwarf plant height, its short leaf internodes resulting in a dense crown with an upright form, its large leaves, its dark bronze trunks with exfoliating bark, its ease of propagation by tissue culture, and its hardiness to U.S.D.A. Zone 2.

3 Drawing Sheets

Botanical classification: *Prunus maackii.*
Variety denomination: 'Jefspur'.

BACKGROUND OF THE INVENTION

The present invention relates to a new and distinct cultivar of *Prunus maackii,* and will be referred to hereafter by its cultivar name, 'Jefspur'. 'Jefspur' a new cultivar of amur cherry tree grown for use as a landscape plant.

The new cultivar of amur cherry, 'Jefspur', was discovered by the inventor in June of 1998 in Saskatoon, Saskatchewan, Canada as a naturally occurring whole plant mutation. 'Jefspur' was selected as a single unique plant grown among a group of seedlings planted in an urban landscape that were derived from unnamed plants of *Prunus maackii.*

Asexual reproduction of the new cultivar was first accomplished by in vitro propagation under the direction of the inventor in Kelowna, British Columbia, Canada in March 2004. The characteristics of this cultivar have been determined to be stable and are reproduced true to type in successive generations.

SUMMARY OF THE INVENTION

The following traits have been repeatedly observed and represent the characteristics of the new cultivar as grown outdoors in a test plot for eight years in Saskatoon, Saskatchewan, Canada. These attributes in combination distinguish 'Jefspur' as a unique cultivar of amur cherry.

1. 'Jefspur' has a dwarf plant size, reaching 3.6 to 4.6 m (12 to 15 ft) in eight years whereas the species typically reaches 6 to 7.6 m (20 to 25 ft) in cultivation in the same time period.
2. 'Jefspur' has a compact growth habit with leaf internodes that are 40 to 50% shorter than is typical for the species and other cultivars known to the inventor.

3. 'Jefspur' exhibits forms a very dense crown with an upright form.
4. 'Jefspur' exhibits larger leaves than the species.
5. 'Jefspur' exhibits exfoliating bark that is darker bronze in color in comparison to the species.
6. 'Jefspur' is readily propagated by tissue culture.

'Jefspur' is unique and unlike any other cultivars of amur cherry known to the inventor. In addition to the differences to the parent species, *Prunus maackii,* 'Jefspur' can also be compared to the cultivar 'Jefree' (not patented). 'Jefspur' differs from 'Jefree' in having a denser crown, shorter leaf internodes, larger leaves, and bark that is lighter in color.

BRIEF DESCRIPTION OF THE DRAWING

The accompanying colored photographs illustrates the overall appearance and distinct characteristics of the new amur cherry as grown in trial sites in Saskatoon, Saskatchewan, Canada.

The photograph is FIG. 1 was taken of an eight year-old tree of 'Jefspur' and illustrates its compact, upright growth habit.

Figure 1:
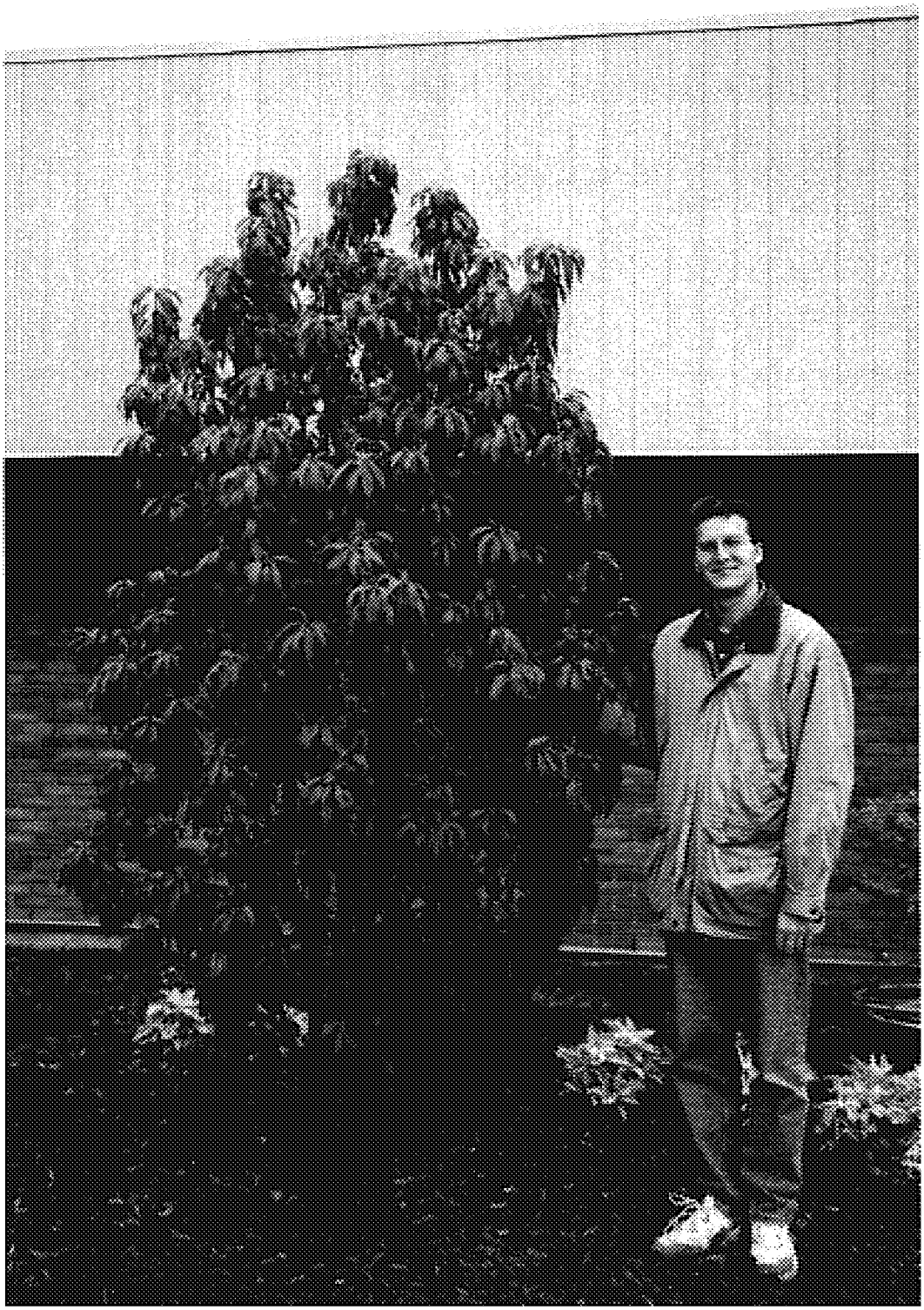
Figure 2:
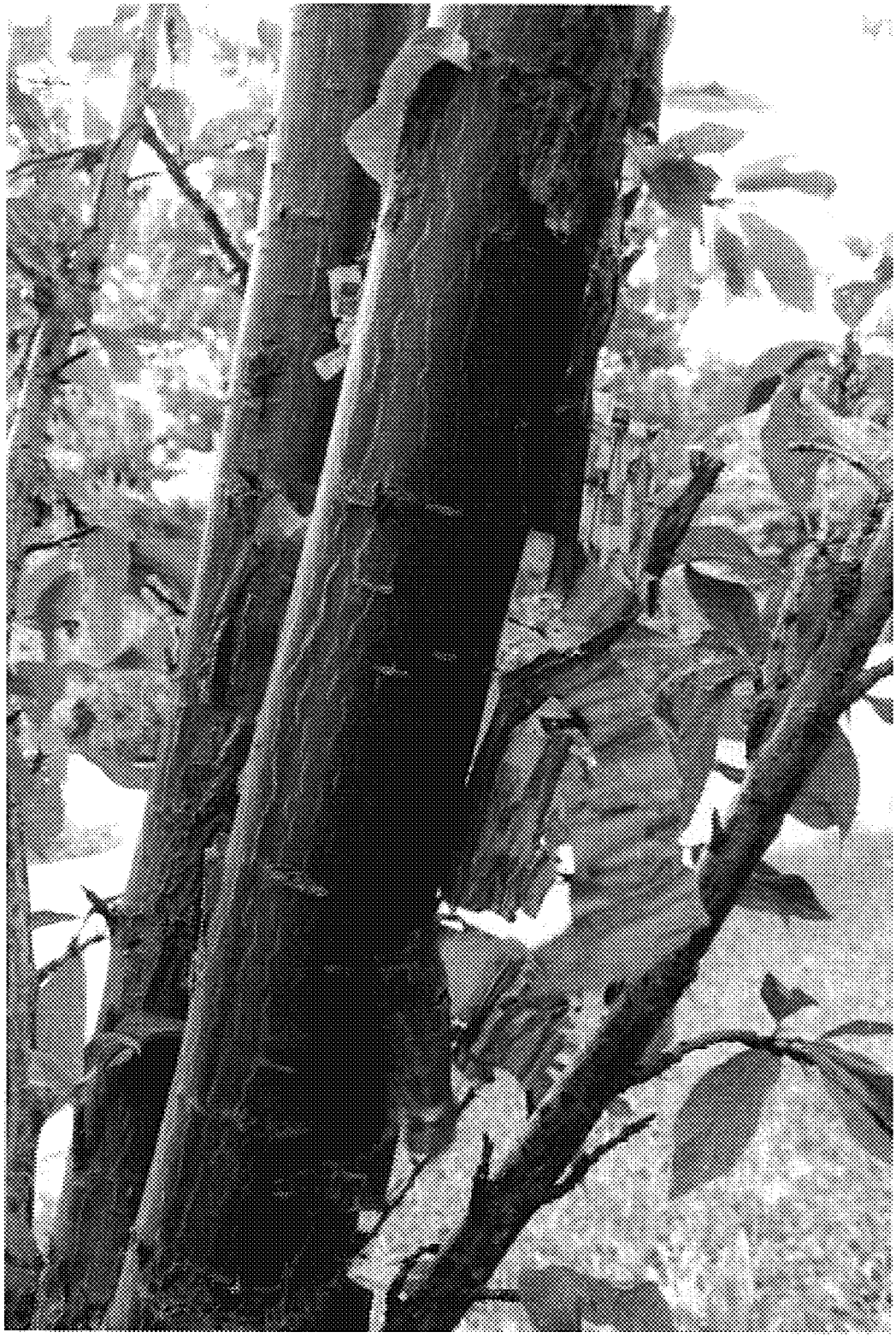

The photograph in FIG. 2 was taken of a tree about 8 years in age and provides a close-up view of the leaves and mature bark of 'Jefspur'.

Figure 3:
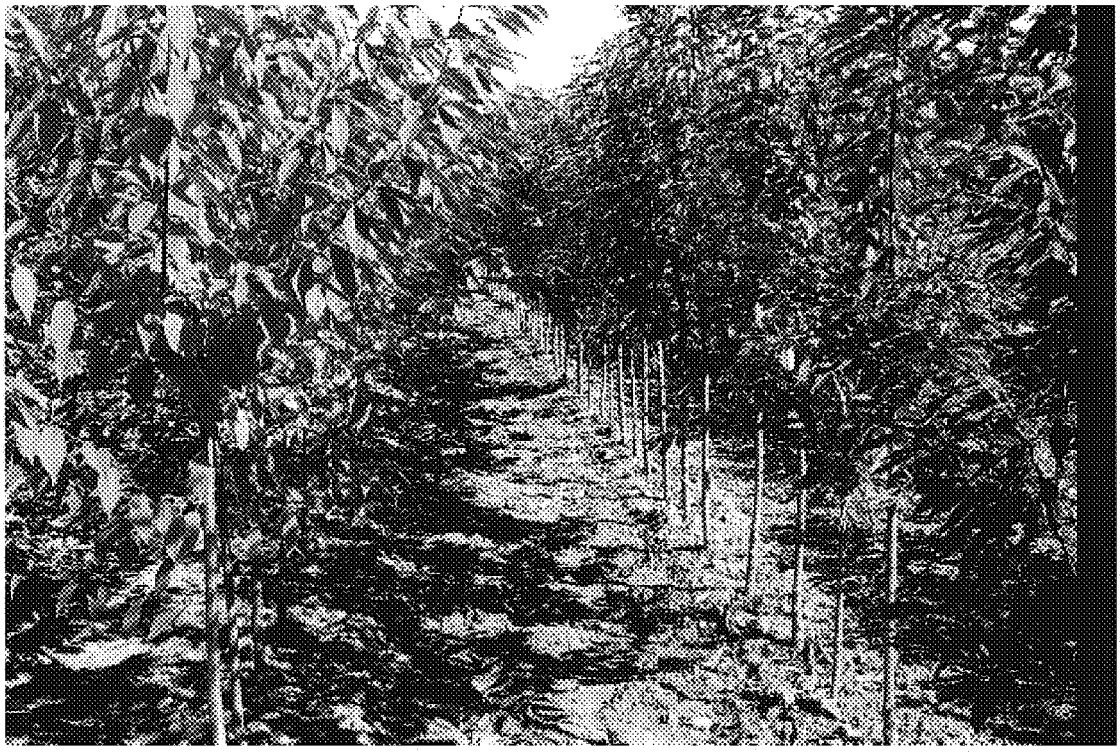

The photograph in FIG. 3 provides a comparison of two year-old trees of 'Jefspur' (row of trees on right) when grown under the same conditions as 'Jefree' (row of trees on left).

Figure 4:
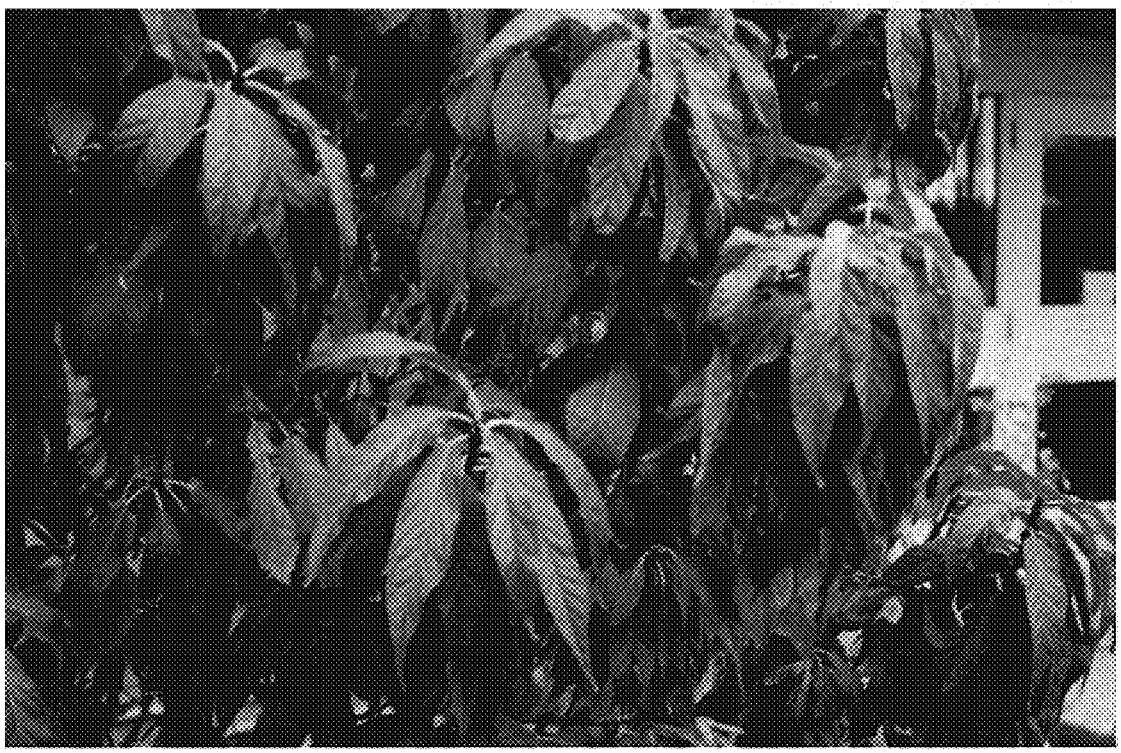

The photograph in FIG. 4 shows a close-up view of the foliage on a tree eight years in age.

The colors in the photograph are as close as possible with the digital photography techniques available, the color values cited in the detailed botanical description accurately describe the colors of the new amur cherry.

DETAILED BOTANICAL DESCRIPTION

The following is a detailed description of an 8 year-old trees of the new cultivar as grown outdoors in Manitoba, Canada. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Botanical classification.*—'Jefspur' is a whole plant mutation of an unknown cultivar of *Prunus maackii.*

*Blooming period.*—Blooms from approximately May 15 to May 25th in Portage la Prairie, Manitoba.

*Plant habit.*—Compact, forms a dense crown with an upright form.

*Height and spread.*—Reaches about 3 to 3.6 m (10 to 12 ft) in height and about 1.5 m in width (5 ft.).

*Cold hardiness.*—U.S.D.A. Zone 2.

*Diseases and pests.*—No susceptibility or resistance to diseases or pests has been observed.

*Root description.*—Fibrous, freely branched.

*Propagation.*—Tissue culture or softwood stem cuttings (30% rooting success).

*Growth rate.*—Moderate.

Stem description:

*Shape.*—Twigs slightly oval.

*Stem color.*—New growth 138A, maturing twigs 177A, bark; color between 166B and 166C with lenticels and striations of 198A and peeling bark 164C suffused with 166C.

*Stem size.*—Trunk; 6 cm in diameter measured 10 cm above soil level, lateral branches average about 2 cm in diameter and 75 cm in length on a tree 8 years in age.

*Stem surface.*—Twigs glabrous with slight gloss, mature wood covered with papyraceous bark.

*Branch internode length.*—Average of 2.6 cm.

Foliage description:

*Leaf shape.*—Elliptic.

*Leaf division.*—Simple.

*Leaf base.*—Cuneate.

*Leaf apex.*—Acuminate.

*Leaf fragrance.*—None.

*Leaf venation.*—Pinnate, not prominent or conspicuous, same as leaf color with the midrib on lower surface 145A.

*Leaf margins.*—Finely serrate.

*Leaf arrangement.*—Alternate.

*Leaf attachment.*—Petiolate.

*Leaf substance.*—Typical for *Prunus macckii* cultivars.

*Leaf surface.*—Glabrous on upper and lower surface.

*Leaf size.*—Mature leaves average 12 cm in length and 4.4 cm in width.

*Leaf internodes.*—Average of 2.5 cm on first year growth and 1.3 cm on second year growth.

*Leaf color.*—Newly expanded leaves upper surface; between 138A and 144A, newly expanded leaves lower surface; between 138B and 144A, mature leaves upper surface; 137B, mature leaves lower surface; between 138A and 138B, fall color is nondescript with leaves dropping early.

*Petioles.*—Average of 1.8 cm in length and 1.5 mm in width, 138A in color, concave on upper surface, glabrous surface.

*Stipules.*—2 per leaf, average of 7 mm in length and 1 mm in width, linear in shape, 138B in color with glandular margins 177A in color.

Inflorescence description:

*Inflorescence type.*—Raceme of approximately tightly congested flowers on upper nodes.

*Inflorescence size.*—Average of 5.5 cm in length and 2 cm in width.

*Flower buds.*—Oblanceolate in shape with apex comprised of sharp tips of sepals, up to 8 cm in length and 2.2 cm in width prior to opening, 144A in color.

*Flower fragrance.*—None detected.

*Flower quantity.*—About 22 per inflorescence.

*Flower aspect.*—Held at about a 45° angle.

*Flower type.*—Rotate corolla above an elongated calyx with stamens and pistil extended.

*Flower size.*—Average of 1.2 cm in diameter and 1 cm in depth.

*Calyx.*—Comprised of sepals fused into an ovoid base with un-fused portions spreading at apex.

*Sepals.*—5, 144A in color, glabrous surface, about 6 mm in length with un-fused portions about 2 mm in width and length, entire glandular margin, attenuate apex and fused base.

*Petals.*—5, oblong in shape, un-fused, thin and papery substance, entire margin, oblique base, broadly acute apex, about 5 mm in length and 2 mm in width, whiter than N155C in color (upper and lower surface).

*Pedicels.*—Average of 5 mm in length, <0.1 mm in width, 144A in color, glabrous surface.

*Rachis.*—About 4 cm in length, 1.5 mm in width, 144A in color, glabrous surface, flowers lightly compacted with whorled arrangement.

Reproductive organs:

*Gynoecium.*—1 pistil about 1 cm in length and 0.3 mm in width extending beyond perianth, style is 144A in color at base and 145D near apex, about 8.5 mm in length and 1 mm in length, stigma is about 0.3 mm in diameter and about 161A in color, ovary is superior and 144A in color.

*Androecium.*—Average of 17 stamens, base adnate to calyx, filaments are 155A in color, about 4 mm in length and 0.3 mm, anthers are 162B in color, dorsifixed, about 0.5 mm in length and in width, pollen is abundant and about 165B in color.

*Fruit and seed.*—Fruit a pruinose drupe and 5 mm in length and 4 mm in width with single seed 202A in color.

It is claimed:

1. A new and distinct cultivar of amur cherry tree named 'Jefspur' as herein illustrated and described.

* * * * *